(12) United States Patent
Margaria

(10) Patent No.: US 6,391,255 B1
(45) Date of Patent: May 21, 2002

(54) METALLURGICAL-GRADE SILICON WITH A CONTROLLED STRUCTURE FOR USE IN HALOSILANE SYNTHESIS

(75) Inventor: Thomas Margaria, Passy (FR)

(73) Assignee: Pechiney Electrometallurgie, Courbevoie (FR)

( * ) Notice: Subject to any disclaimer, the term of this patent is extended or adjusted under 35 U.S.C. 154(b) by 0 days.

(21) Appl. No.: 09/155,343

(22) PCT Filed: Mar. 24, 1997

(86) PCT No.: PCT/FR97/00514

§ 371 Date: Jan. 28, 1999

§ 102(e) Date: Jan. 28, 1999

(87) PCT Pub. No.: WO97/36821

PCT Pub. Date: Oct. 9, 1997

(30) Foreign Application Priority Data

Apr. 2, 1996 (FR) ............................................. 96 04378

(51) Int. Cl.$^7$ ................................................. C22C 35/00
(52) U.S. Cl. ........................................ 420/578; 420/590
(58) Field of Search ................................ 420/578, 590; 148/405

(56) References Cited

U.S. PATENT DOCUMENTS

| | | | | | |
|---|---|---|---|---|---|
| 2,380,995 A | * | 8/1945 | Rochow | ...................... | 260/607 |
| 5,068,385 A | * | 11/1991 | Degen et al. | ................ | 556/472 |
| 5,182,091 A | * | 1/1993 | Yuge et al. | .................. | 423/348 |
| 5,605,583 A | * | 2/1997 | Margaria | ..................... | 148/405 |
| 5,714,131 A | * | 2/1998 | Margaria et al. | ............ | 423/348 |

FOREIGN PATENT DOCUMENTS

EP 0 673880 A1 * 2/1995 ........... C01B/33/02

* cited by examiner

Primary Examiner—Roy King
Assistant Examiner—Harry D. Wilkins, III
(74) Attorney, Agent, or Firm—Connolly Bove Lodge & Hutz

(57) ABSTRACT

A metallurgical-grade silicon for use in alkyl or aryl halosilane synthesis, and having a structure consisting of primary silicon crystals and intermetallic compounds, particularly of silicon, aluminum and calcium, wherein at least 90% of the primary silicon crystals have an aluminum content of 50–1000 ppm. This structure substantially enhances the reactivity of the silicon in the synthesis reaction.

3 Claims, No Drawings

METALLURGICAL-GRADE SILICON WITH A CONTROLLED STRUCTURE FOR USE IN HALOSILANE SYNTHESIS

TECHNICAL FIELD

The invention relates to a particular quality of metallurgical silicon with a controlled structure and containing aluminum, intended particularly for synthesis of alkyl or aryl-halogenosilanes used in the manufacture of silicones.

Metallurgical silicon is silicon obtained industrially by carbothermal reduction of silica in an electric furnace. It contains at least 98% silicon, and the other main elements are iron, aluminum and calcium. It also contains some oxygen and other elements such as P, Ti, V, Ni, etc., with a content of <0.1%.

STATE OF THE ART

The synthesis of alkyl or aryl halogenosilanes by the reaction of a halogenated hydrocarbon on silicon at a temperature of between 250 and 350° C. in the presence of a catalyst has been known since U.S. Pat. No. 2,380,995 issued to Rochow in 1945.

Rochow's reaction has been developed industrially to a large extent because it is the basis of the silicones industry. It is usually used with methyl chloride $CH_3Cl$ and gives a mix of different methyl chlorosilanes, particularly monomethyl-trichlorosilane (denoted by the letter T) and dimethyl-dichlorosilane (denoted by D). Since the required product is D, it is important to carry out the reaction so that a maximum proportion of D is obtained in the resulting mix of silanes, this proportion being called the selectivity of the reaction. It is also important to produce the maximum quantity of silanes per unit time, the value of the weight of silanes produced per unit time being called the reactivity.

A large amount of work has been carried out to improve the reactivity and selectivity of the reaction. In particular, the role played by intermetallic compounds present in the structure of the metallurgical silicon used as a raw material has been emphasized. For example the publication by the applicant T. MARGARIA, J. C. ANGLEZIO and C. SERVANT "Intermetallic Compounds in Metallurgical Silicon" at the INFACON 6 conference, Proceedings of the $6^{th}$ International Ferroalloys Congress, Cape Town, vol. 1, 1992, published by SAIMM, Johannesburg, pages 209–214, indicates the various intermetallic compounds present in the silicon and the means of controlling them. DE 4037021 by ELKEM recommends the presence of some ternary or quaternary phases containing Si, Fe, Al and Ca.

It is also known that the structure of intermetallic compounds located at silicon grain joints can be modified to improve the reactivity and selectivity of the Rochow reaction. These types of structures were proposed in Wacker chemie's EP 0610807, and the applicant's EP 0673880.

However, regardless of the care taken in forming, analyzing and structuring these intermetallic compounds, they are always located at the surface of the silicon grains, such that they are only effective at the beginning of the reaction.

Therefore, the applicant looked for a means of improving the reactivity and selectivity of the reaction by acting on the silicon grains themselves. This can be done by checking their phosphorus content, as described in WO 95/01303 deposited by BAYER and the applicant. However, the silicones industry continues to require silicon capable of further increasing the selectivity and reactivity of the Rochow reaction.

SUMMARY OF THE INVENTION

The object of the invention is a metallurgical silicon intended to be used for the synthesis of alkyl and aryl halogenosilanes, the structure of which is composed of primary silicon crystals and intermetallic compounds based essentially on silicon, iron, aluminum and calcium, and is characterized in that more than 90% of the primary silicon grains have an aluminum content of between 50 and 1000 ppm. This structure is preferably obtained with a silicon with a global aluminum content by weight of between 0.12 and 0.30%, and with a silicon solidification process after casting capable of dropping below 1200° C. in less than 10 seconds.

DESCRIPTION OF THE INVENTION

In particular, since silicon is used as a semiconductor in electronic applications, it is known that the solubility of most elements in solid silicon is very low; the solubility of aluminum is of the order of 15 ppm. When metallurgical silicon obtained in the liquid state is solidified, the excess quantity of aluminum that cannot pass into solid solution in the primary silicon collects at grain joints in the form of secondary intermetallic compounds with a high aluminum content.

The applicant has found that for a given range of aluminum contents and under particular conditions for solidification of the liquid silicon, it is possible to increase the aluminum content of the primary silicon crystals beyond the normal saturation limit of 15 ppm, and to control the super-saturation level by adjusting the content of aluminum in the liquid silicon and its solidification rate, in order to increase the reactivity of silicon in the Rochow reaction.

One way of measuring the aluminum content in solid solution in primary silicon is to use an ionic probe (SIMS= Secondary Ion Mass Spectrometry). According to one normal method, when SIMS is used for a quantitative analysis, a sensitivity factor RSF is determined for aluminum such that the concentration C (in atoms per $cm^3$) is equal to the product $RSF \times I_{Al}/I_{Si}$, in other words the product of the sensitivity factor by the ratio of measured intensities for aluminum and the silicon matrix.

This RSF factor is obtained by taking the average of at least five measurements made on pre-implanted standards with a known concentration, and is of the order of $3.3 \cdot 10^{23}$.

The super-saturation level of aluminum in primary silicon increases with the aluminum content in the initial liquid silicon and with the solidification rate. Thus, if 4 mm thick silicon is cast on a water cooled copper plate, resulting in complete solidification in less than 10 seconds, the following values are obtained (by weight):

| % Al in liquid Si | ppm Al in primary Si crystal |
| --- | --- |
| 0.10 | 110 |
| 0.15 | 150 |
| 0.20 | 260 |

By reducing the cast thickness to 2 mm, which results in complete solidification in less than 2.5 s, the following values are obtained:

| % Al in liquid Si | ppm Al in primary Si crystal |
| --- | --- |
| 0.10 | 130 |
| 0.15 | 250 |
| 0.20 | 490 |

Experience also shows that the results obtained depend mainly on the cooling rate between the liquid state (about 1415° C.) and 1200° C., the cooling rate between 1200° C. and the ambient temperature not having very much influence. These operating conditions are completely different from the conditions mentioned in BAYER's EP 0617039, which recommends fast cooling between 700° C. and 120° C. Thus, of removing solid silicon from the mold when the silicon is still red after casting on a water cooled copper plate does not significantly modify the level of super-saturation in aluminum in silicon crystals, compared with removal of the silicon from the mold at ambient temperature.

Furthermore, the cooling rate, particularly between 1400 and 1200° C., also affects the percentage of primary silicon crystals with an aluminum content exceeding 50 ppm, very high rates giving more than 95% of super-saturated crystals, or even percentages close to 100%.

Examination with an electron scanning microscope and by X-ray diffraction of silicon crystals super-saturated in aluminum shows the existence of deformations in the crystals, such as dislocations or shear planes. For a constant content of intermetallic compounds and with an identical content of phosphorus in the primary silicon, it is observed that the reactivity of silicon super-saturated in aluminum is higher than that obtained with a silicon for which the crystals contain the normal content of about 15 ppm in solid solution. The improvement in reactivity is not very significant below a content of 50 ppm of aluminum in the crystal. It is difficult to exceed a super-saturation rate of 1000 ppm, since the aluminum then crystallizes separately.

Under industrial solidification conditions capable of changing from the liquid state to below 1200° C. in less than 10 seconds, these limits correspond to a total content of aluminum in the liquid silicon between 0.12 and 0.30% by weight.

EXAMPLE

A liquid silicon with the following composition (by weight)

Fe=0.35% Ca=0.70% Al=0.60% Ti=0.022% P=90 ppm was produced by carbothermy in an electric furnace using silicon and a carbonated reducing agent.

This silicon was then refined in the ladle by the addition of silica and the injection of oxygen to lower the Ca and Al contents. The analysis of the refined silicon was as follows:

Fe=0.38% Ca=0.056% Al=0.15% Ti=0.022% P=90 ppm

This ladle was then cast:
a) firstly on a casting installation consisting of two water cooled copper cylinders rotating in opposite directions as described in the applicant's EP 0057651, in which the cylinder rotation speed was adjusted to obtain a 4 mm thick strip. Sample No. 1 was then taken from the silicon cast in this way.
b) partly in a 10 mm thick conventional cast ingot mold. Sample No. 2 was taken from this silicon.

An analysis of the two samples gave the following results:

|  | No. 1 | No. 2 |
| --- | --- | --- |
| Fe | 0.37% | 0.38% |
| Al | 0.15% | 0.15% |
| Ca | 0.056% | 0.054% |
| Ti | 0.022% | 0.022% |
| P | 90 ppm | 90 ppm |
| P in primary Si | 90 ppm | 90 ppm |
| Al in primary Si | 260 ppm | 15 ppm |
| % Si$_2$Al$_2$Ca | 0 | 0 |

A methylchlorosilane production test was carried out on each of the samples under the following conditions:

The tests were carried out in a 30 mm diameter glass reaction vessel with stirred bed, equipped with a stirrer. The same quantity of silicon was used in each test, with the same distribution of particles between 70 and 160 $\mu$m. The reaction mix consisted of 40 g of silicon, 3.2 g of partially oxidized copper as a catalyst and 0.05 g of ZnO.

Methyl chlorine was added to the reaction mix through a sintered glass disk at a pressure of 0.2 MPa. After heating the reaction medium and starting the reaction, the system temperature was adjusted and kept at 300° C. and the quantity and composition of the silanes mix formed was determined.

The values are summarized in the following table, in which P denotes the total quantity of silanes produced in g/h; MeH, Mono, T, D, PS denote the percentages by weight of monomethyldichlorosilane ($CH_3HSiCl_2$), trimethylchlorosilane (($CH_3)_3SiCl$), methyltrichlorosilane ($CH_3SiCl_3$), dimethyldichlorosilane (($CH_3)_2SiCl_2$) and polysilanes respectively. Since the required product is dimethyldichlorosilane, the selectivity of the reaction is evaluated by D, whereas the reactivity is measured by P. The values shown are the averages of 4 individual measurements.

| Sample | P | MeH | Mono | T | D | T/D | PS |
| --- | --- | --- | --- | --- | --- | --- | --- |
| 1 | 7.2 | 2.5 | 2.9 | 4.5 | 90.1 | 0.050 | 4.6 |
| 2 | 6.8 | 2.0 | 2.5 | 4.9 | 90.3 | 0.054 | 5.2 |

It can be seen that sample 1, in which the primary silicon is super-saturated in aluminum, has a 6% better reactivity while the selectivity has only changed by 0.2%.

What is claimed is:

1. Metallurgical silicon for the synthesis of alkyl or arylhalogenosilanes, the structure of which is composed of primary silicon crystals and intermetallic compounds based on silicon, iron, aluminum and calcium, wherein at least 90% of said primary silicon crystals have an aluminum content of between 50 ppm and 1000 ppm i.e., beyond the normal saturation limit of 15 ppm.

2. Metallurgical silicon according to claim 1, wherein its total content of aluminum by weight is between 0.12% and 0.30%.

3. A process for manufacturing metallurgical silicon according to claim 1, comprising the steps of (a) preparation of a liquid silicon bath by reduction of silica in an electric furnace by a carbonated reducing agent, (b) refining of said silicon bath, and (c) cooling the liquid silicon from a liquid state to less than 1200° C. in less than 10 seconds.

* * * * *